United States Patent
Strohmaier

(10) Patent No.: US 6,540,892 B1
(45) Date of Patent: Apr. 1, 2003

(54) SENSOR FOR DETERMINING THE CONCENTRATION OF GAS COMPONENTS IN A GAS MIXTURE

(75) Inventor: Rainer Strohmaier, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/662,583

(22) Filed: Sep. 15, 2000

(30) Foreign Application Priority Data

Sep. 15, 1999 (DE) .......................................... 199 44 181

(51) Int. Cl.$^7$ ............................................ G01N 27/407
(52) U.S. Cl. ..................... 204/408; 204/424; 219/497
(58) Field of Search ................................. 204/408, 406, 204/424, 425, 426, 427, 428, 429; 219/499, 497

(56) References Cited

U.S. PATENT DOCUMENTS

| | | | |
|---|---|---|---|
| 4,694,809 A | * | 9/1987 | Nakano et al. ............. 123/684 |
| 4,875,990 A | * | 10/1989 | Kodachi et al. ............ 204/408 |
| 5,214,267 A | | 5/1993 | Hoshi et al. |
| 6,022,464 A | | 2/2000 | Schumann |
| 6,228,252 B1 | * | 5/2001 | Miyata et al. .............. 205/781 |
| 6,258,232 B1 | * | 7/2001 | Hasegawa et al. .......... 204/424 |
| 6,304,813 B1 | * | 10/2001 | Ikeda et al. ................. 123/697 |

FOREIGN PATENT DOCUMENTS

| | | |
|---|---|---|
| DE | 4408504 | 9/1995 |
| EP | 0482366 | 4/1992 |
| WO | WO 95/25277 | 9/1995 |

* cited by examiner

Primary Examiner—Robert J. Warden, Sr.
Assistant Examiner—Kaj K. Olsen
(74) Attorney, Agent, or Firm—Walter Ottesen

(57) ABSTRACT

A sensor determines the concentration of gas components in a gas mixture with at least one measuring electrode exposed to the gas mixture and a reference electrode and with a heating device for controlling the temperature of at least one measuring electrode and the reference electrode. A measurement signal taken off the at least one measuring electrode can be changed via a corrective value, which is dependent upon the heating power of the heating device necessary to reach a pregiven value of the heating resistance of at least one heating element of the heating device.

5 Claims, 1 Drawing Sheet

SENSOR FOR DETERMINING THE CONCENTRATION OF GAS COMPONENTS IN A GAS MIXTURE

FIELD OF THE INVENTION

The invention relates to a sensor for determining the concentration of gas components in a gas mixture. Such a sensor is especially suitable for monitoring the operability of catalytic converters in the exhaust-gas decontaminating systems of internal combustion engines.

BACKGROUND OF THE INVENTION

Internal combustion engines generate exhaust gas which contains, inter alia, carbon monoxide, nitrogen oxide as well as uncombusted or partially combusted hydrocarbons. Measurements of the oxygen content in exhaust gases carried out with conventional lambda probes do not by themselves always provide sufficient data as to the quality of the combustion of the fuel mixture. For different applications, it is especially important to be able to control the oxidizable gas components occurring with incomplete combustions. In addition to reducing the limit values of the exhaust-gas emissions, the monitoring of the catalytic converter in exhaust-gas systems with respect to its function, such as in on-board diagnostics, is gaining greatly in significance.

Here, sensors are increasingly being used which are based on the mixture potential principle. Such sensors are, for example, disclosed in U.S. Pat. No. 6,022,464 as well as in German patent publication 4,408,504. The measurement principle of such sensors requires a very precise control of the temperature of the measurement electrodes. For this purpose, a heater control is used which uses the resistance of the heating device, which is integrated into the solid electrolyte of the sensor, directly as a temperature signal. The heater device is, for example, the resistance of a platinum heating device.

SUMMARY OF THE INVENTION

It is an object of the invention to provide an improvement of the temperature control for the measuring electrodes of a gas sensor based on the mixture potential principle.

A systematic error arises in sensors of this kind in that the temperature measurement does not take place at the location of the measuring electrodes but spatially separate therefrom on the heater resistor. Accordingly, it is still another object of the invention to be able to correct especially this systematic error.

The sensor arrangement of the invention is for determining the concentration of a gas component in a gas mixture. The sensor arrangement includes: a sensor including: at least one measuring electrode exposed to the gas mixture and from which a measurement signal is tapped; a reference electrode disposed in spaced relationship to the measuring electrode; and, a heater device having a heater element; and, a circuit unit including means for generating and supplying heating power to the heater element in an amount required to reach a pregiven value of the heater resistance of the heating element; and, means for generating a corrective value for changing the measurement signal in dependence upon the heating power.

By changing the measurement signal by a corrective value, a significant improvement of the correlation between the measurement signal of the sensor and the concentration of the exhaust-gas component to be measured is achieved.

The corrective value is dependent upon the heating power of the heating device which is required to arrive at a pregiven value of the heater resistance. The exhaust-gas component is measured for different measuring parameters and/or at different operating points of an engine whose gas mixture is detected.

According to an advantageous embodiment of the invention, the corrective value for changing the measuring signal can be determined in dependence upon the change of the heating power by a measurement during operation and can be stored in a characteristic field. In this way, the functional relationship of the corrective value can be determined exactly and can be used to correct the measurement signal. The functional relationship is dependent upon the temperature dependency of the sensor signal.

In another advantageous embodiment of the invention, the corrective value is directly proportional to the change of the heating power. In this case, a corrective value need only be determined by measurement.

The sensor arrangement for determining the concentration of a gas component in a gas mixture includes: a sensor including: at least one measuring electrode exposed to the gas mixture and from which a measurement signal is tapped; a reference electrode disposed in spaced relationship to the measuring electrode; and, a heater device having a heater element having a resistance having a pregiven desired value; and, a circuit unit including means for increasing the desired value of the resistance at an operating point of the sensor having an increased heating power requirement so that a temperature drop associated with the increased heating power requirement is compensated with the temperature drop being to the at least one measuring electrode.

In this embodiment, the temperature at the electrode is held constant instead of correcting the temperature influence on the signal. In this way, the systematic error can also be corrected. The systematic error occurs in such sensors in that the temperature measurement is not made at the location of the measuring electrodes but is made at the heater resistor separated spatially from the measuring electrodes. Here, it is advantageous to determine the desired value by measurements in different operating states of the sensor and to store the same in a characteristic field.

The desired value is determined in dependence upon the temperature drop to the measuring electrodes with the temperature drop being detected via measurement.

BRIEF DESCRIPTION OF THE DRAWING

The invention will now be described with reference to the single FIGURE (FIG. 1) of the drawing, which shows a sensor, in section, according to an embodiment of the invention.

DESCRIPTION OF THE PREFERRED EMBODIMENT OF THE INVENTION

Figure 1:
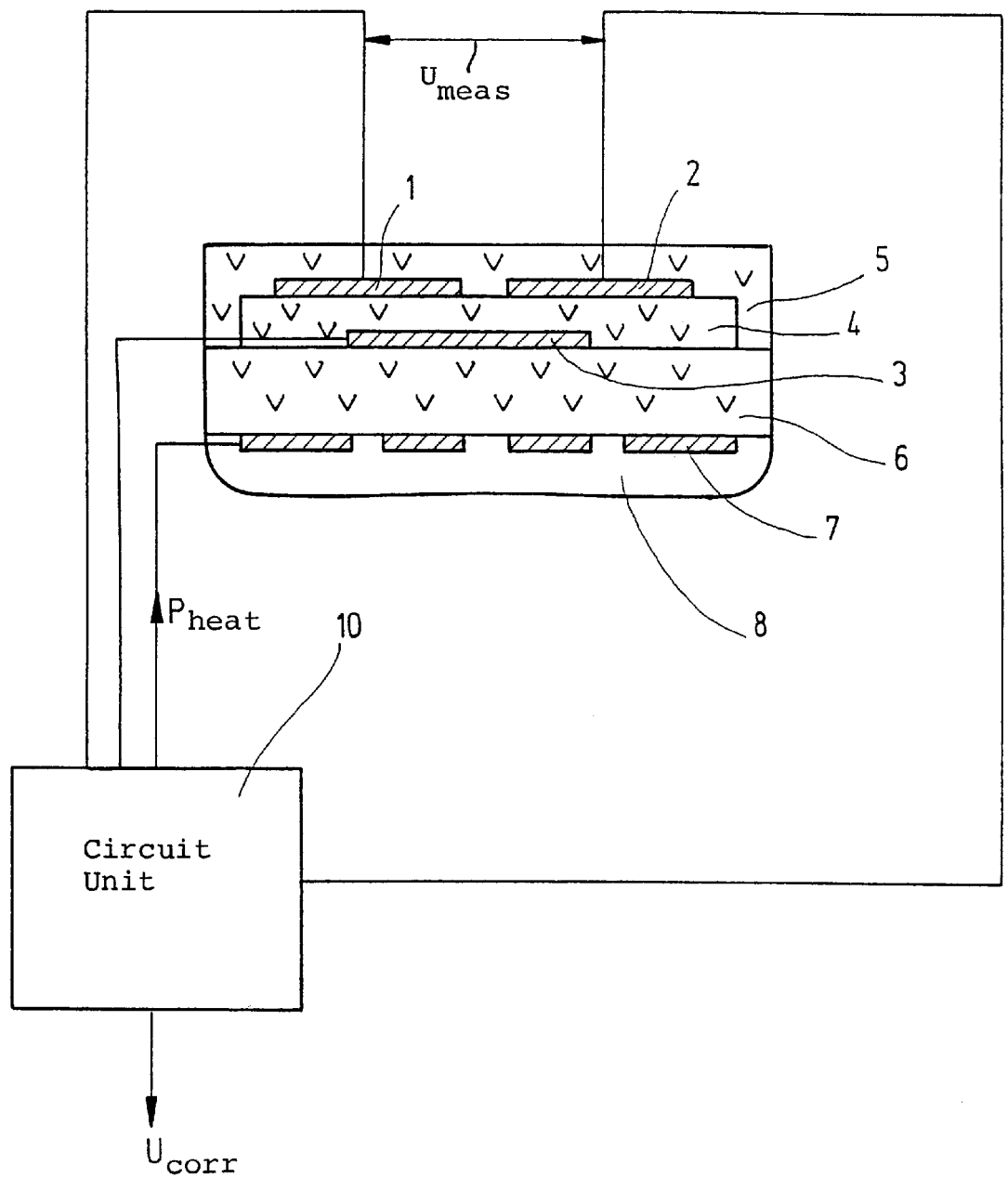

The sensor shown in FIG. 1 includes an insulating planar ceramic substrate 6. Several layers lie one atop the other on a large surface of the substrate 6. These layers carry a reference electrode 3 made, for example, of platinum, a solid electrolyte 4, measuring electrodes 1 and 2 and a gas-permeable protective layer 5. A heater device 7 having a cover 8 is arranged on the opposite-lying large surface of the substrate 6.

The sensor is heated by the heating device 7 to a temperature of between 300° and 1000° C. for determining the concentration of oxidizable constituents in gas mixtures, for example, exhaust gases of an internal combustion engine. The sensor is advantageously heated to 600° C.

The protective layer 5 can be sintered to be porous in order to make possible the diffusion of the gas to be measured to the reference electrode 3 and to make possible the adjustment of the oxygen equilibrium potential. Furthermore, a reference channel or a reference gas atmosphere (not shown) can be provided in a manner known per se.

At least on one of the measuring electrodes (1, 2), the sensor generates a measurement signal across the oxygen-ion conducting solid electrolyte 4 in the form of a cell voltage via a first half-cell reaction, which is adjusted with the aid of the reference electrode 3, and a second half-cell reaction, which is affected by the oxidizable gas components to be determined. The concentrations of the gas components are determined in a circuit unit 10 via calibration curves from voltage values. In the simplest case, the sensor according to the invention can be used with a reference electrode 3 which catalyzes the equilibrium adjustment of the gas mixture and a measuring electrode 1 or 2 which do not or only slightly catalyze the equilibrium adjustment of the gas mixture.

As shown in FIG. 1, it is, however, also possible to arrange two measuring electrodes 1 and 2 or even several measuring electrodes having respectively different catalytic activity for adjusting oxygen equilibrium states. The measuring electrodes 1 and 2 then react with a different voltage referred to the reference electrode 3. This voltage is dependent upon the type of gas.

In arrangements with two or several measuring electrodes (1, 2) having different catalytic activity, the possibility is also present to evaluate voltages between the measuring electrodes (1, 2) for determining oxidizable gases. In addition, the Seebeck effect is eliminated in voltage measurements between measuring electrodes which are arranged in the same plane and at the same distance to the heating device 7 such as the measuring electrodes 1 and 2 shown in FIG. 1. With an arrangement having at least two measuring electrodes (1, 2), the further possibility is present as shown in FIG. 1 to compensate the cross sensitivity of a first measuring electrode 1 completely or at least partially utilizing the signal of a further measuring electrode 2 in that the sensitivity of this additional measuring electrode 2 is adjusted in correspondence to the disturbing gas components.

A very precise control of the temperature of the measuring electrodes (1, 2) is required for measuring specific exhaust-gas components such as hydrocarbons. For this purpose, a control of the heating device 7 is provided which uses the resistance of the heating element directly as a temperature signal. The heating element is integrated into the sensor and is, for example, a platinum heating element.

During steady-state operation, a heat current or flow $\Phi$ flows between the heating element of the heating device 7 and the sensor surface cooled by the exhaust gas. A heating resistance R is between the heating element of the heating device 7 and the measuring electrodes (1, 2) arranged on the sensor surface. Depending upon this heating resistance R, a temperature difference $\Delta T$ is present which is determined as follows:

$$\Delta T = R * \Phi.$$

The heating power $P_{heat}$ must be adapted to the changed cooling power of the exhaust gas when the temperature or the volume flow of the exhaust gas changes in order to hold the temperature of the heating device 7 constant. For this reason, the flow of heat through the sensor changes and therefore also the temperature difference $\Delta T$. The temperature of the measuring electrodes (1, 2) is therefore dependent upon the cooling capacity of the exhaust gas also when the temperature of the heating device 7 is held constant. The signal of the mixture potential sensors exhibits great dependency upon temperature. For this reason, a correction of the sensor signal is required; that is, a correction of the voltage signal $U_{meas}$ which can be taken off between the measurement electrodes 1 and 2 or of the voltage signal $U_{meas}$ which can be taken off between the measurement electrode 1 and the reference electrode 3 or between the measurement electrode 2 and the reference electrode 3.

The basic idea of the invention is to use the heater power $P_{heat}$ for the purpose of correcting the sensor signal. The heater power $P_{heat}$ is that heating power which is required for the heater resistance of the heater element to reach its desired value. The change of the heater power $\Delta P_{heat}$, which is required in order to compensate a changed cooling power, is directly proportional to the change of the temperature of the measuring electrodes (1, 2). An actuating quantity of the heater control can therefore be used directly as an input signal for correcting the measuring signal $U_{meas}$ as shown in the following equation:

$$U_{corr} = U_{meas}(1 - f(P_{heat})).$$

The functional relationship $f(P_{heat})$ is dependent upon the temperature dependency of the measuring signal $U_{meas}$ and has to be determined experimentally via measurements on the sensor which is in operation, that is, when used in the exhaust-gas system of a vehicle during the operation of the engine. The functional relationship $f(P_{heat})$ can, for example, be stored in a characteristic field.

In one embodiment, a linear approximation is assumed and the corrective signal $U_{corr}$ is directly proportional to the measurement signal $U_{meas}$ less a corrective value which corresponds to the heating power $\Delta P_{heat}$ as follows:

$$U_{corr} = U_{meas}(1 - K * \Delta P_{heat}).$$

The corrective factor K must be determined experimentally via measurements of the sensor, which is in operation, and therefore the engine which is in operation. The corrective factor K can be the subject matter of a characteristic line.

The correction of the measuring signal takes place in the circuit unit 10. A significant improvement of the correlation between the measuring signal of the sensor and the concentration of the exhaust-gas component to be measured is achieved by utilizing the actuating quantity signal of the control of the heating device 7 for the correction of the dependency of the sensor signal on the temperature and the volume flow of the exhaust gas. The significant improvement of the correlation between the measurement signal of the sensor and the concentration of the exhaust-gas components is at different operating points of the sensor or at different operating points of the engine in whose exhaust-gas channel the sensor is located.

In another embodiment, the temperature at the electrodes (1, 2) is to be held constant instead of correcting the temperature influence on the signal. For this purpose, the desired value of the heater resistance of the heating element of the heating device 7 is so increased at operating points of the sensor having increased heating power requirement, that a larger drop associated therewith to the measurement electrodes (1, 2) is compensated. It is understood that the temperature drop must be determined in advance experimentally.

The desired value is advantageously stored in dependence upon the operating conditions in a characteristic field.

It is understood that the foregoing description is that of the preferred embodiments of the invention and that various changes and modifications may be made thereto without departing from the spirit and scope of the invention as defined in the appended claims.

What is claimed is:

1. A sensor arrangement for determining the concentration of a gas component in a gas mixture having a cooling power which changes in response to changes of volume flow or temperature thereof, the sensor arrangement comprising:

a sensor including: at least one measuring electrode exposed to said gas mixture and from which a measurement signal is tapped; a reference electrode disposed in spaced relationship to said measuring electrode; and, a heater device including a heater element having a heater resistance; and, a circuit unit including means for generating and supplying heating power, adapted to said cooling power, to said heater element in an amount required to reach a pregiven value of the heater resistance of said heating element; and, means for generating a corrective value for changing said measurement signal in dependence upon said heating power adapted to said cooling power.

2. The sensor arrangement of claim 1, wherein said corrective value is determined in dependence upon a change of said heating power by measurement during the operating state of said sensor and is stored in a characteristic field.

3. The sensor arrangement of claim 1, wherein said corrective value is directly proportional to the change of the heating power.

4. The sensor arrangement of claim 1, wherein said corrective value is determined by measurement in the operating state of said sensor and is stored in a characteristic line.

5. A sensor arrangement for determining the concentration of a gas component in a gas mixture having a cooling power which changes in response to changes of volume flow or temperature thereof, the sensor arrangement comprising:

a sensor including: at least one measuring electrode exposed to said gas mixture and from which a measurement signal is tapped; a reference electrode disposed in spaced relationship to said measuring electrode with said temperature being measured at a location of said sensor remote from said electrodes; and, a heater device having a heater element having a resistance having a pregiven desired value; and, a circuit unit including means for increasing said desired value of said resistance so that a temperature drop, which is associated with an increased heating power requirement at an operating point of said sensor, is compensated for to said at least one measuring electrode with said heating power requirement being adapted to said cooling power of said gas mixture; and, said desired value being determined by measurement in the operating state of said sensor and is stored in a characteristic field.

* * * * *